United States Patent [19]

Paolino

[11] Plant 4,520

[45] Apr. 15, 1980

[54] ROSE PLANT—MEIGANDOR VARIETY

[75] Inventor: Marie-Louise Paolino, Antibes, France

[73] Assignee: The Conard-Pyle Company, West Grove, Pa.

[21] Appl. No.: 968,840

[22] Filed: Dec. 12, 1978

[30] Foreign Application Priority Data

Dec. 28, 1977 [BE] Belgium ..... 862431

[51] Int. Cl.[2] ..... A01H 5/00

[52] U.S. Cl. ..... Plt./22

[58] Field of Search ..... Plt./16, 22, 25

*Primary Examiner*—Robert E. Bagwill

*Attorney, Agent, or Firm*—Burns, Doane, Swecker & Mathis

[57] ABSTRACT

A rose-plant of the Floribunda Class is provided having double flowers which are of orpiment color on the inside and yellow on the outside. The seed parent of the new variety was obtained by the crossing of the variety Sweet Promise (known in the United States as Sonia) and the variety Golden garnette. The pollen parent of the new variety resulted from the crossing of the variety Meialfi and the variety Meifan to form a first plant which was crossed with the variety King's ransom to form a second plant which in turn was crossed with the variety Whisky mac.

16 Drawing Figures

SUMMARY OF THE INVENTION

The object of the present invention is to provide a new variety of rose-plant of the Floribunda Class which is distinguished from prior varieties by the following characteristics:

(1) from the physical point of view, the plant with light green adult wood is erect, produces double flowers which are of orpiment color on the inside and yellow on the outside, has rounded petals which are leathery in texture, and dull foliage which is relatively ample and moderately dense; and (2) from the biological point of view has vigorous vegetation, a great tendency to force, produces flowers of long duration both when cut and on the plant, and average resistance to disease.

In view of these characteristics the new variety meets the needs of the horticultural industry for all purposes, and particularly is suited for the production of cut flowers.

The new variety was created by artificial pollination whereby two genitors which previously had been studied for the possession of the characteristics sought in the new variety were combined.

The seed parent of the new variety was obtained by the crossing of the variety Sweet promise (known in the United States as Sonia — U.S. Plant Pat. No. 3,095) and the variety Golden garnette (U.S. Plant Pat. No. 1,898). The pollen parent of the new variety resulted from the crossing of the variety Meialfi and the variety Meifan to form a first plant which was crossed with the variety King's ransom (U.S. Plant Pat. No. 2,103) to form a second plant which in turn was crossed with the variety Whiskey mac.

This parentage of the new variety may be expressed as follows:

(Sweet promise × Golden garnette) × (( (Meialfi × Meifan) × King's ransom) × Whisky mac).

The seeds resulting from the above pollination were sown and 128 plantlets were obtained which were physically and biologically different from each other. Selective study resulted in the identification of a single plant of the new variety. Extensive testing has confirmed the behavior and characteristics of the new variety which is particularly suited for the production of cut flowers.

The characteristics and properties of the new variety have been found to be transmissible by agamic means, also called "asexual", i.e. by means of vegetative propagation, in particular by grafting an eye. The rose-plant of the new variety has been designated the Meigandor variety.

BRIEF DESCRIPTION OF THE FIGURES

The accompanying photographs show under glass at Antibes, France as nearly true as it is reasonably possible to make the same in a color illustration of this character, typical specimens of the cut flowers and foliage, illustrated in.

Figures 1, 2, 3, 4, 5, 6, 7, 8, 9, 10, 10B, 11, 12, 13, 14, 15, 16:
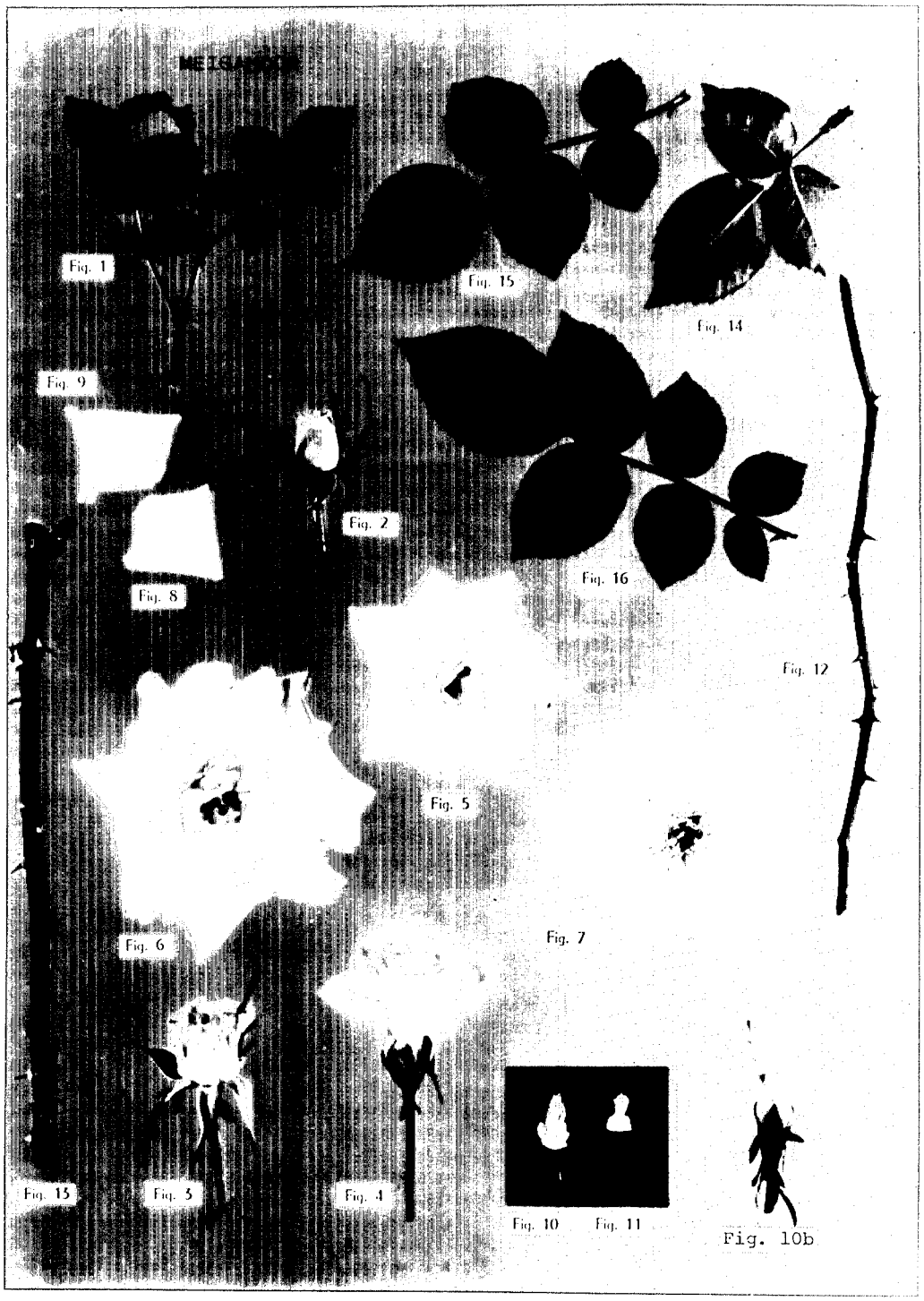
FIG. 1 — a specimen of a young shoot.
FIG. 2 — a specimen of a bud at the opening of the sepals.
FIG. 3 — a specimen of a bud at the opening of the petals.
FIG. 4 — a specimen of a flower in the course of opening.
FIG. 5 — a specimen of a flower in the course of opening — plan view — obverse.
FIG. 6 — a specimen of an open flower — plan view — obverse.
FIG. 7 — a specimen of a flower in full bloom — plan view — obverse.
FIG. 8 — a specimen of a petal, obverse.
FIG. 9 — a specimen of a petal, reverse.
FIG. 10 — a specimen of a receptacle showing the arrangment of the stamens and of the pistils.

FIG. **10*b*** — a specimen of a receptacle showing the arrangement of a vegetative center;

FIG. 11 — a specimen of a receptacle showing the arrangement of pistils (stamens removed);

FIG. 12 — a specimen of a flowering twig;

FIG. 13 — a specimen of a main branch;

FIG. 14 — a specimen of a leaf with 3 leaflets — under surface;

FIG. 15 — a specimen of a leaf with 5 leaflets — upper surface; and

FIG. 16 — a specimen of a leaf with 7 leaflets — upper surface.

DETAILED DESCRIPTION

The plant described was grown under glass at Antibes, France.

The chart utilized in the identification of the colors is that of the Royal Horticultural Society (R.H.S. Colour Chart). The terminology preceding the numbered references to this chart has been added to designate in common terms the corresponding colors.

Class: Floribunda.

Plant:

*Height.*—On the basis of the cutting back in greenhouses to 0 m. 80 cm., the length of the cut stems reaches between approximately 40 and 50 cm.

Branches:

*Color.*—Young stems: before the bud is formed they are light green. The leaves are light green, very slightly reddish purple on the edge of the folioles. Mature wood: light green 137/C (green group).

*Prickles.*—Shape — upper edge: straight, inflected towards the base. Lower edge: concave. Base: elliptic. Size: medium. Quantity: from average to numerous. Multiple acicules. Color — on young stems: initially reddish purple, then they become straw yellow. On mature wood: Havana brown.

Leaves:

*Stipules.*—Adnate, pectinate, they are narrow, small and serrulated.

*Petioles.*—Inner surface: the deeper part of the groove is light green, the edges slightly glandular. Outer surface: light green with hooked prickles.

*Folioles.*—Number: 3 or 5 or 7. Shape: oval base, symmetrical and wide. Tip: symmetrical and pointed. Teeth: single and coarse. Texture: leathery. General effect: relatively ample, moderately dense and dull.

*Color.*—Young foliage: Upper surface: light green 137/C (green group). The teeth are slightly reddish purple. Under surface: greenish grey 191/C (greyed green group). Adult foliage: Upper surface: medium green 137/A (green group). Under surface: greenish grey 191/B (greyed green group).

Inflorescence:

*Number of flowers.*—Several per stem.

*Peduncle.*—Erect, rigid, light green. Medium length of approximately 85 mm.

*Sepals.*—Whitish and tomentous inside and light green outside. Tapered and narrow tip. The edges occasionally have a few appendages.

*Bud.*—Shape: when the sepals burst open, the edges of the bud are straight and the tip flattened out. Length: outside the calyx approximately 25 mm. Size: small. Color: When opening: The outside of the petals appears to be tangerine 24/A (orange group) and the unguis is yellow, slightly greenish on the level of the median vein.

*Flower.*—Shape: on opening the bud has straight edges, with the lower part being flat. The flower opens slowly, first in full cup, then in hollow cup letting the heart come into sight. The flowers are double. Diameter: approximately 105 mm. on the average when disbudded, but ordinarily is approximately 80 mm. Color: At the opening: Inside: orange 28/A (orange group). Yellow unguis largely marked. Outside: tangerine 24/B (orange group). Slightly reddish on the edge of the petal. The yellow unguis is greenish on the level of the median vein. While opening: Inside: Carrot red 29/A (orange group), going to orpiment 25/A (orange group), and to deep yellow for the unguis which is lightly marked. Outside: medium yellow 15/B (yellow orange group) becoming lighter towards the center and the tip of the petal in 16/D (yellow orange group). When fully open: Inside: Salmon 27/B (orange group) for the center of the petal, getting lighter at the top. Yellow at the level of the unguis. Outside: very light yellow 11/D (yellow group); unguis deeper yellow. Fragrance: slight. Lasting quality: very long, on the plant as well as when cut. Corolla: Petals:Texture: Leathery. Shape: Wide base. The petal is very much rounded at the top. The center petals are not always entire. The outer petals are slightly reflexed, in a point. Number: approximately 25 to 30. Shedding petals: The petals drop off cleanly. Stamens: Numbers: Approximately 50 on the average. Anthers: Normal and yellow. Filaments: Long and yellow. Pistils: Number: approximately 25 to 30 on an average. Stigmas: Yellow; reach the same height as the anthers. Styles: Long, whitish at the base, and fuchine at top. Fairly often they are modified at the vegetative center. Light green and going amply beyond the stamens. Receptacle: light green, hairless, when cut longitudinally, wide and in the shape of a funnel.

Development:

*Vegetation.*—Vigorous.

*Blossoming.*—Continuous under glass.

*Resistance to disease.*—Average.

I claim:

1. A new and distinct variety of Floribunda rose-plant characterized by the fact that from the physical point of view, the plant with light green adult wood is erect, produces double flowers which are of orpiment color on the inside and yellow on the outside, has rounded petals which are leathery in texture, and dull foliage which is relatively ample and moderately dense; and from the biological point of view has vigorous vegetation, a great tendency to force, produces flowers of long duration both when cut and on the plant, and average resistance to disease;

substantially as shown and described.

* * * * *